United States Patent
Strähle et al.

[11] Patent Number: 6,142,988
[45] Date of Patent: Nov. 7, 2000

[54] ZOOM SYSTEM FOR A LASER SLIT LAMP

[75] Inventors: Fritz Strähle, Heubach; Peter Schäffer, Oberkochen, both of Germany

[73] Assignee: Carl-Zeiss-Stiftung, Germany

[21] Appl. No.: 08/732,025

[22] Filed: Oct. 16, 1996

[30] Foreign Application Priority Data

Oct. 16, 1995 [DE] Germany .......................... 195 38 412

[51] Int. Cl.[7] ...................................................... A61N 5/06
[52] U.S. Cl. .................................. 606/4; 606/10; 359/691
[58] Field of Search ..................... 606/2, 3–19; 359/676, 359/677, 686, 689, 691

[56] References Cited

U.S. PATENT DOCUMENTS

| | | | |
|---|---|---|---|
| 2,428,122 | 9/1947 | Montani | 359/691 |
| 2,784,644 | 3/1957 | Bednarz | 359/691 |
| 3,703,176 | 11/1972 | Vassiliades et al. | 606/4 |
| 4,397,310 | 8/1983 | Pomerantzeff | 606/4 |
| 4,576,445 | 3/1986 | Inadome . | |
| 5,336,216 | 8/1994 | Dewey . | |

OTHER PUBLICATIONS

Zeiss "Visulas Argon 11" Brochure.

*Primary Examiner*—David M. Shay

[57] ABSTRACT

The invention relates to a zoom system for imaging, with a variable scale of imaging, a fixed entrance plane (16) onto a likewise fixed target plane (15). The zoom system includes a proximal partial system ($T_1$) with variable converging power and a distal partial system with fixed converging power. The proximal partial system itself includes a distal component (10) and a proximal component (8), which respectively have a positive converging power. The converging power of the proximal component (8) is substantially greater than the converging power of the distal component (10). The proximal partial system ($T_1$) acts as a collimator. The rear focal plane is virtual. Between the proximal component (8) and the distal component (10), two components (9a, 9b) with negative converging power are displaceable along the optical axis for varying the magnification. These displaceable components (9a, 9b) have a high converging power, so that a large variation of the imaging scale between 1× and 20× can be attained with short displacement paths. The zoom system preferably serves for focusing a therapy laser beam in a laser slit lamp. Due to the high converging powers in the proximal portion of the zoom system, the laser beam is greatly widened, and the beam waist is located behind the target plane (15), by which means high intensities in the front region of the eye are avoided.

16 Claims, 4 Drawing Sheets

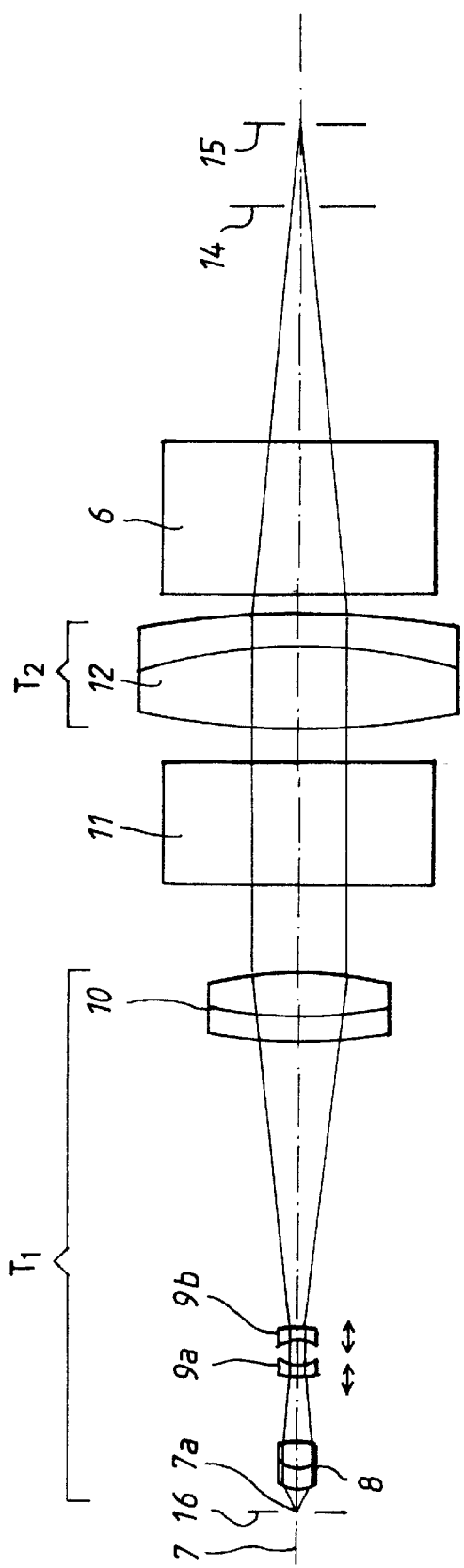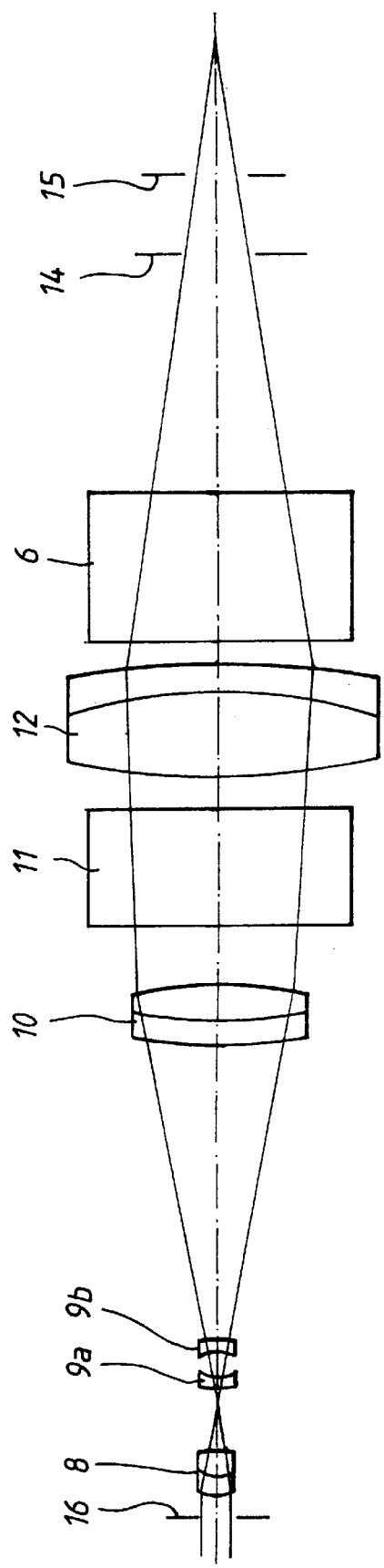

β = 1

β = 10

β = 20

ZOOM SYSTEM FOR A LASER SLIT LAMP

BACKGROUND OF THE INVENTION

1. Field of the Invention

The present invention relates to a Zoom System for imaging a laser beam onto a target plane.

2. Description of Prior Art

A laser slit lamp for photocoagulation is offered, for example, under the designation "VISULAS Argon II", and is described, for example, in the Carl Zeiss brochure with the printer's imprint 30-374-D (W-TS-I/92 T 00). In this system, the laser beam is conducted via a glass fiber to the slit lamp of the slit lamp microscope, and is coupled via a subsequent optical system into the illuminating beam path. The optical system subsequent to the glass fiber images the exit face of the glass fiber onto the retina to be treated. In this case the light bundle exiting the fiber end contains both the therapy beam, for example that of an argon laser, and also a weak, visible targeting beam, for example that of a laser diode.

The optical system, for imaging the exit face of the glass fiber, firstly contains a collimator which collimates the divergent beam bundle leaving the glass fiber. For this purpose the exit face of the glass fiber is arranged in the focal plane of the collimator. The collimated beam bundle is expanded by a succeeding afocal Galilean pancratic lens with a variable telescopic magnification, and is finally focused by an objective, at the focal point of the objective. Consequently an image of the exit face of the glass fiber results at the focal point of the objective. The diameter of this image is, according to the adjustment of the Galilean pancratic lens, between 50 μm and 500 μm. Here, the exit face of the glass fiber has a diameter of 50 μm, that is, the fiber end is imaged with a magnification between 1× and 10×. The particular range of magnification in which the exit face of the fiber is sharply imaged on the retina is termed the "parfocal" range.

A further enlargement of the spot diameter on the retina can be obtained in the so-called defocused mode, in which the image of the fiber end is defocused by an intentional offset adjustment of the afocal Galilean pancratic lens, that is, the image of the exit face of the fiber lies behind the retina. However, this defocused mode, in contrast to the parfocal range, an intensity distribution corresponding to a Gaussian bell curve is obtained, instead of a rectangular intensity profile in the parfocal range. Such a Gaussian intensity profile is unfavorable, however, for clinical application. Apart from this, this defocused mode is concommitant with a very long and very slender beam waist of the laser beam, so that beam intensities arise in the region of the cornea that under unfavorable circumstances, and with simultaneous non-compliance with predetermined limits to settings of the laser power, can lead to corneal damage. The energy of the laser beam is concentrated in a smaller cross sectional area in the region of the slender beam waist thereby increasing the energy density, i.e., intensity. Because this beam waist (having increased energy density) is long it probably includes the cornea. But because the cornea must not be exposed to high energy densities the long and slender beam waist of the defocused mode and therefore the defocused mode is potentially harmful to the cornea.

An optical system for a laser slit lamp is known from U.S. Pat. No. 5,336,216, in which a real intermediate image of the fiber end is produced by a short-focus, two-component system. The size of the intermediate image is variable by changing the distance between the two short focus components. However, an axial displacement of the intermediate image accompanies the variation of the size of the intermediate image. The real intermediate image is imaged at a 1:1 scale on the retina by means of a subsequent long focus system of two components, of which the first is coupled to the movement of the short focus system.

The result achieved by this system is that, at all spot diameters between 50 μm and 1,200 μm on the retina, the beam has a large cross section, and thus a low intensity, in the plane of the cornea. However, this optical system, at spot diameters between 500 μm and 1,200 μm, must be operated in the so-called defocused mode, that is, for spot diameters of this size the exit face of the glass fiber has to be imaged behind the retina. A further disadvantage of this known solution is its very considerable length, which excludes a compact integration of the optical system into a slit lamp. Moreover, the required displacement paths of the zoom system are very large, so that it is mechanically expensive to make. A main problem in this solution is, furthermore, that one of the short focus components is brought, in the defocused mode, into the plane of the intermediate image of the fiber end, which can result in problems because of the high power densities at this point.

Furthermore, zoom objectives for cameras are known, for example, from U.S. Pat. No. 4,576,445, which have two lens groups with overall positive converging power, and two subsequent lens groups with negative converging power. In them, the components with negative converging power are movable to vary the magnification. However, such photographic objectives are not suitable for use in laser slit lamps, because of their optical construction and because of the usually only small zoom factor of 3 to 4.

SUMMARY OF THE INVENTION

The present invention has as its object to provide a zoom system which images an exit plane into an image plane and with which a zoom factor of more than 10× between the minimum and maximum magnification can be attained.

This object is attained, according to the invention, by a zoom system for imaging a laser beam from a fixed entrance plane onto a target plane with a variable imaging scale, in which the zoom system has a proximal partial system ($T_1$) with a variable converging power and a distal partial system ($T_2$) with a fixed converging power. The rear focal plane of the proximal partial system ($T_1$) is virtual, and has a focal point distance (BA) that is substantially greater than its focal length. Advantageous embodiments of the invention will become apparent from the detailed description of the invention.

The zoom system according to the invention has, like the system of the "VISULAS Argon II" described at the beginning, a proximal partial system with a variable converging power, with a spatially fixed proximal focal plane, and a distal partial system, with a fixed converging power. In contrast to the prior art system, the proximal partial system contains, instead of three, only two components with positive converging power: one proximal and one distal. A further difference from the prior art system is that the converging power of the proximal component is substantially larger than the converging power of the distal component, and that the whole proximal partial system is designed as a collimator. At the same time, the exit side (rear) focal point distance of the proximal partial system is substantially larger than its focal length, and the rear focal point is virtual.

The exit plane of the laser beam can be embodied as the end face of a glass fiber, and lie in the entrance plane of the zoom system, which at the same time is the front focal plane of the proximal partial system. A divergent beam emerging from this entrance plane leaves the proximal partial system as a collimated light beam and is focused by the distal partial system in its rear focal plane. If the retina to be treated lies in this rear focal plane, the end face of the glass fiber is then imaged on the retina.

If the variable focal length of the proximal partial system is denoted by $f_1$ and the fixed focal length of the distal partial system by $f_2$, the imaging scale of the zoom system is $\beta=f_2/f_1$. With a scale change (zoom factor) from $\beta=1$ to 20, the focal length $f_1$ of the proximal system varies from $f_2$ to $f_2/20$.

For laser beams, the imaging of the fiber end face is also denoted as imaging of the near field, and the imaging of the beam waist of the laser beam is denoted as imaging of the far field. The imaging of the beam waist of the laser beam can be approximately described by a parallel beam entering the zoom system.

The arrangement of the proximal and distal components is such that at all zoom factors the rear focal point distance of the proximal partial system is substantially larger, that is, larger by a factor of at least 10–50, than the respective focal length of the proximal partial system. As a consequence of the short focal length of the proximal component, a beam entering parallel to the optical axis is greatly widened within the proximal component, and leaves the proximal partial system, because of the virtual position of the rear focal point, as a beam which is slightly divergent and nearly parallel. Due to the great widening of this beam because of the high converging power of the proximal component, the beam is strongly convergent before reaching the beam waist, so that the intensity correspondingly greatly diminishes with increasing distance from the beam waist.

To change the focal length of the zoom system, the proximal component preferably has a lens, or a lens element, with positive converging power, and two lenses or lens elements which are displaceable parallel to the optical axis and which have negative converging power. The entrance plane is then spaced from the lens, or lens element, which has a positive converging power, by more than the focal length of the latter, so that the beam path behind this lens element with positive converging power runs convergingly, and a divergence which is required corresponding to the desired magnification can be produced by the displacement of the lens or lens elements with negative converging power. The course of the beam then has no real intermediate imaging of the entrance plane within the zoom system; this is a difference from U.S. Pat. No. 5,336,216, mentioned at the beginning.

The converging power of the proximal component is preferably more than 5 times, more preferably even more than 10 times, the converging power of the distal component, and the lenses or lens elements of the proximal component, both those with positive converging power and those with negative converging power, preferably have a focal length amounting to less than 10 mm. Since only the lenses with negative converging power, and thus correspondingly short focal length lenses, have to be displaced in order to change the scale of imaging, small displacement paths already lead to large changes of the scale of imaging. Overall, a large zoom factor, and at the same time a compact arrangement, can thereby be attained.

When the zoom system according to the invention is used in a slit lamp microscope, the distal partial system of the zoom system is preferably at the same time the objective of the slit illuminating system, and has a focal length between 50 mm and 200 mm, so that a correspondingly large working distance is ensured.

BRIEF DESCRIPTION OF THE DRAWINGS

Preferred embodiments of the invention will be described hereinbelow in further detail, with reference to the accompanying drawings, in which:

FIG. 2A shows a lens section of the zoom system according to the invention, with a beam path drawn in showing near field imaging;

FIG. 2B shows the lens section of FIG. 2A, with a beam path drawn in showing far field imaging;

DETAILED DESCRIPTION OF PREFERRED EMBODIMENTS

Figure 1:
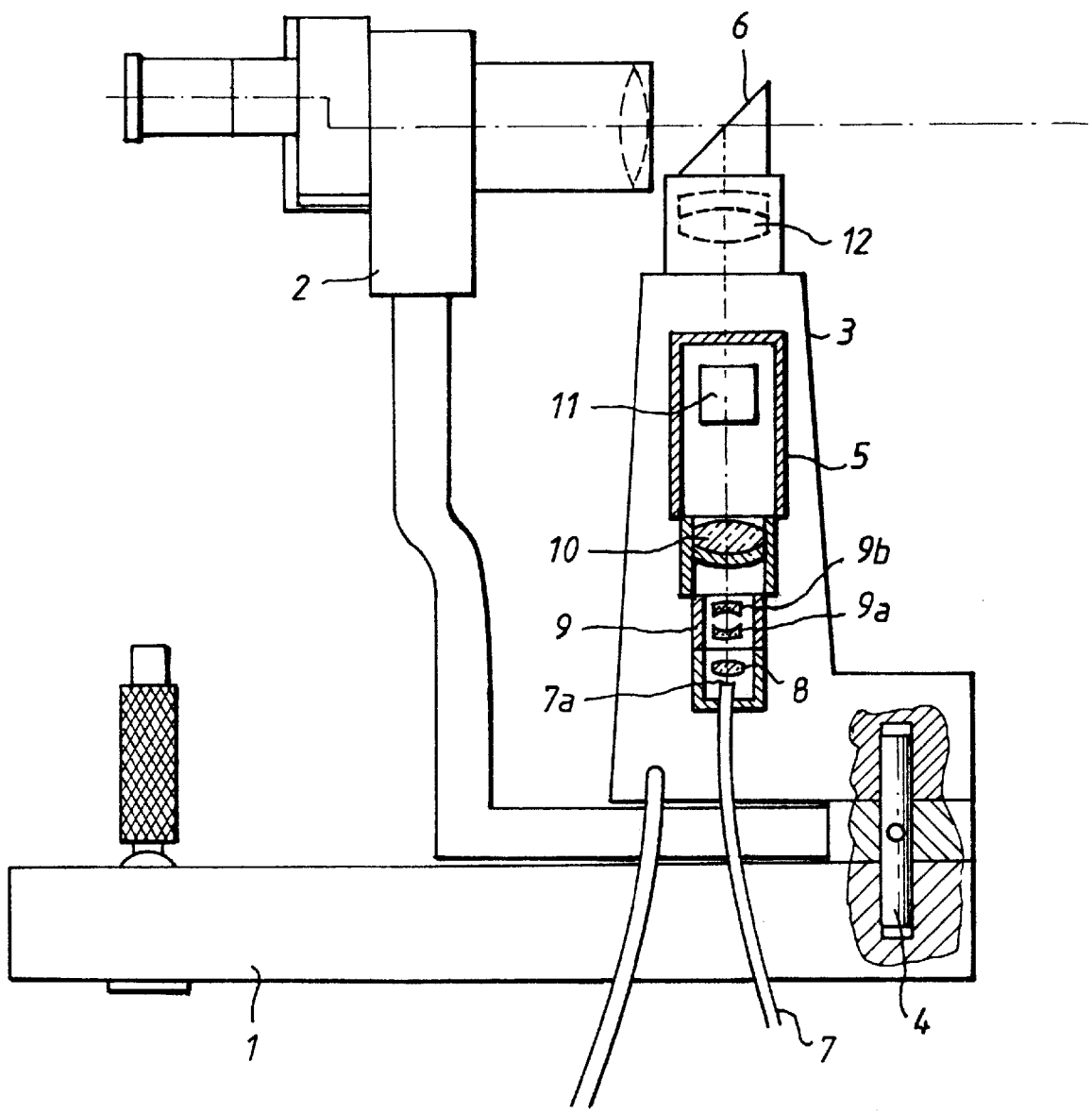
FIG. 1 shows a sectional view of a slit lamp microscope with a zoom system according to the invention.

The slit lamp microscope of FIG. 1 has, in a known manner, an apparatus base (1), on which the microscope body (2) and the slit illuminating system (3) are received and are rotatable about a vertical axis (4) independently of each other. The slit lamp illuminating system, not shown in detail, is for ambient field illumination in the eye to be investigated or treated, and the microscope (2) is for observation of the eye. The adapter for coupling a therapy laser beam into the beam path of the slit illuminating system is denoted by (5). The therapy laser beam itself is fed in to the adapter (5) from a laser (not shown in the drawing), for example an argon laser, via a glass fiber (7), and exits from the end surface (7a) of the glass fiber (7).

The proximal partial system of the zoom system according to the invention is arranged in the adapter (5) and consists of a short focal length, fixedly arranged component (8) with positive converging power, followed by two axially displaceable components (9a, 9b) with negative converging power, and a further stationary component (10) with positive converging power, the converging power of which is substantially smaller than the values of the individual converging powers of the short focus component (8) with positive converging power and the two short focus components (9a, 9b) with negative converging power. The adjusting ring for changing the focal length of the proximal partial system (8, 9a, 9b, 10) is denoted by (9); its rotation brings about, in a known manner, a displacement of the two negative components (9a, 9b) along their optical axis. Since corresponding displaceable mountings for zoom objectives or for microscope objectives with displaceable components are basically known, further details of the specific construction of this mounting will not be more closely described here. Regarding the construction of such mountings, reference is made, for example, to U.S. Pat. No. 4,953,962, which is incorporated by reference.

The laser beam emerging from the proximal partial system is collimated, and the diameter of the beam can be varied by displacement of the components (9a, 9b) with negative converging power. This collimated therapy laser beam is coupled coaxially via a mirror (11) into the beam path, not shown, of the slit illuminating system. The distal partial system (12) of the zoom system is an objective with positive converging power, and is arranged in the united beam path of the therapy laser beam and the slit illuminating system, and serves both for focusing of the therapy laser beam and also for imaging the illuminated slit of the slit illuminating system in the eye which is to be treated or investigated. Behind the distal partial system (12), seen in the beam direction, the previously vertical beam path is deflected by a prism (6) into the horizontal plane, in which the optical axis of the stereomicroscope (2) lies.

The coupling of the therapy laser beam into the beam path of the slit illuminating system requires a very compact design of the zoom system, since the whole length available for the zoom system is smaller than the constructional height of the slit illuminating system.

The optical design of the zoom system is shown in detail in FIGS. 2A and 2B. The short focal length component (8) with positive converging power is a two-lens cemented element with a focal length of 6.2 mm. The two displaceable components (9a, 9b) following it, which are displaceable along the optical axis (shown by a chain line) and have a negative converging power, are two identical plano-concave single lenses with a focal length of −6.6 mm; and the long focal length component (10) following them, of positive converging power, has a focal length of 81.8 mm. These four components form the proximal partial system ($T_1$). The distal partial system ($T_2$) is formed by a two-component cemented element (12) with a focal length of 96.3 mm. This distal partial system ($T_2$) requires a relatively large focal length in the range of values between 50 mm and 200 mm, in order to ensure a sufficiently large working distance to the eye to be treated. The eye to be treated is indicated in FIGS. 2A and 2B by the plane perpendicular to the optical axis at which the optical axis intersects the cornea (plane 14) or the retina (plane 15).

In all zoom positions, the zoom system images the entrance plane (16), which is stationary in space, onto the target plane (15), which is likewise stationary in space, and at the same time is the plane of the retina. Here the imaging scale is variable between 1× and 20×, according to the position of the two plano-concave single lenses (9a, 9b), so that an overall zoom factor of 20× results.

The end face (7a) of the glass fiber (7) is positioned in the entrance plane (16). The distance of this entrance plane (16) from the short focal length component (8) is somewhat larger than the focal length of the short focal length component (8), so that the imaging beam path shown in FIG. 2A runs convergently after emerging from the short focal length component (8). The two single lenses (9a, 9b) with negative converging power diverge the convergent beam path. The reciprocal movement paths of the two lenses (9a, 9b) are set up such that the imaging beam path is always collimated after emerging from the distal component (10) of the proximal partial system ($T_1$), and is consequently imaged in the target plane (15), which lies stationary in space. There results in the target plane (15), due to the sharp imaging, a laser spot with a substantially rectangular intensity profile, perpendicular to the optical axis. The entrance plane (16) coincides, in the arrangement shown, with the front focal plane of the proximal component ($T_1$).

The beam path is shown in FIG. 2B for a beam which enters the zoom system parallel to the optical axis, and approximately describes the far field. This beam is greatly widened in the proximal partial system by the very short focal lengths or large converging powers of the proximal components (8, 9a, 9b).

Since the exit side focal point (17) (see FIG. 2C) is virtual and thus, seen in the direction of the light, lies before the proximal partial system ($T_1$), and has a focal point distance (BA) from the proximal partial system ($T_1$), which is substantially larger than the respective focal length of the proximal partial system, the beam path entering parallel into the zoom system has a slight divergence after emerging from the proximal partial system, and is consequently focused by the distal partial system ($T_2$), in the whole zoom regime, at a distance behind the target plane (15). The beam waist (far field image) of the laser beam lies in this focal plane, which corresponds to the rear focal plane of the zoom system. Due to the great widening of the beam in the proximal partial system, and due to the distance of the beam waist behind the target plane (15), the beam path in the intersection plane (14) with the cornea has a sufficiently large diameter, which is greater than 1 mm in all zoom positions, and thereby a low local intensity. Damage to the cornea is thus largely excluded, even when the prescribed safety rules are disregarded.

Figure 3A:
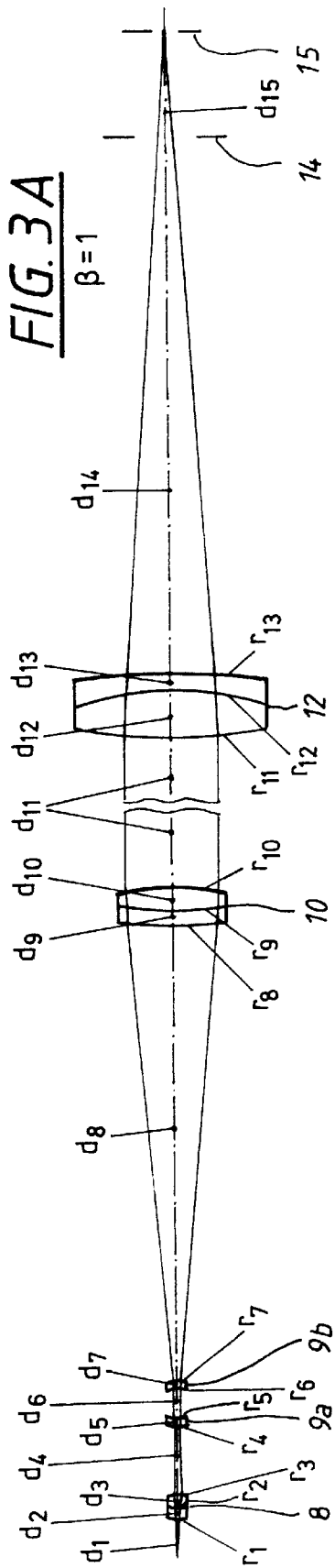
FIG. 3A shows the lens section of the zoom system according to the invention with a magnification of 1×.
Figure 3B:
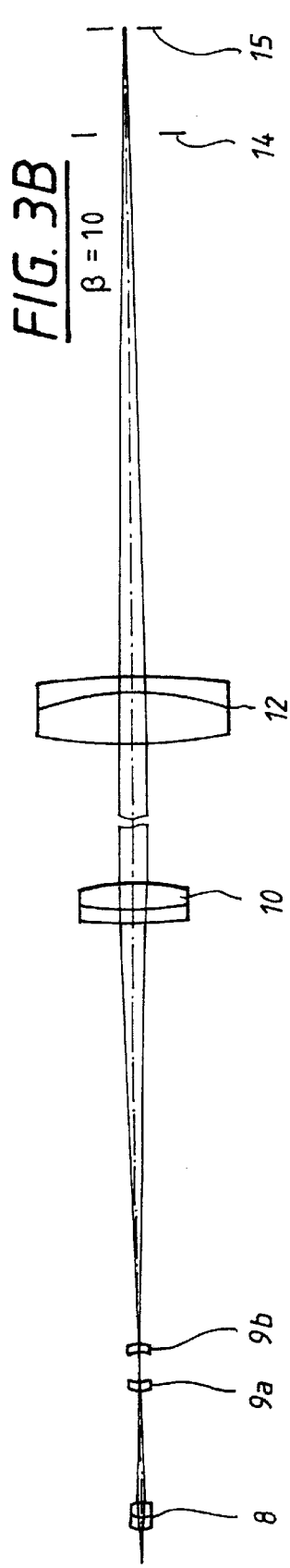
FIG. 3B shows the lens section of the zoom system according to the invention with a magnification of 10×.
Figure 3C:
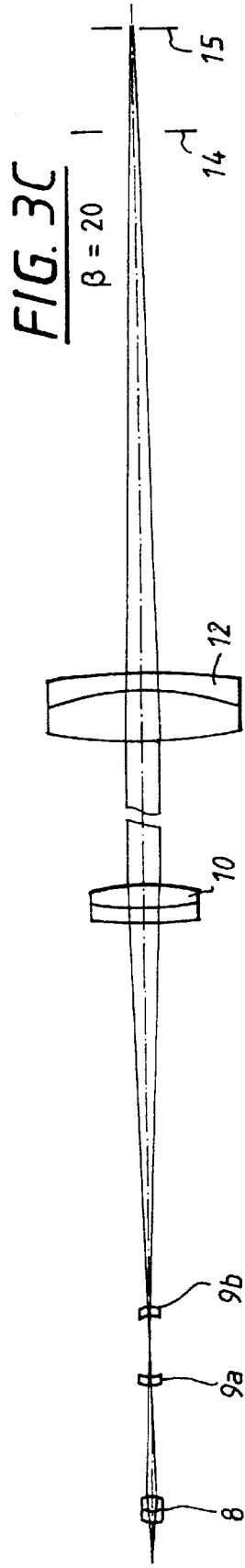
FIG. 3C shows the lens section of the zoom system according to the invention with an imaging scale of 20×.

The zoom system is shown in three different zoom positions in FIGS. 3A–C, without the components, such as the mirror (11) and deflecting prism (6), which do not effect the imaging properties. Likewise, the respective 2w-profile of the laser beam is drawn in, that is, those beams for which the intensity has fallen to $1/e^2$ of the intensity on the optical axis are shown as edge beams. Here the imaging scale in FIG. 3A is $\beta=1\times$, in FIG. 3B, $\beta=10\times$, and in FIG. 3C, $\beta=20\times$. Consequently, with the setting of FIG. 3A, a laser spot with a diameter of 50 μm; in FIG. 3B, with a diameter of 500 μm; and in FIG. 3C, with a diameter of 1,000 μm; is produced in the plane (15) of the retina, for an exit surface of the glass fiber with a diameter of 50 μm. At an enlargement of $\beta=5\times$, that is, with a spot size of 250 μm, the most slender course of the beam results, and hence the highest intensity in the plane (14) of the cornea. At a higher magnification between $\beta=5\times$ and $\beta=20\times$, the course of the beam widens out more, so that the maximum intensity is smaller again.

Even at magnifications of 10× and 20×, no intermediate imaging of the fiber end face or of the entrance plane takes place within the zoom system, that is, even in FIGS. 3B and 3C there is a transition of the beam path between the negative lenses (9a, 9b) from a convergent into a divergent course, without passing through a focus.

Figure 2C:
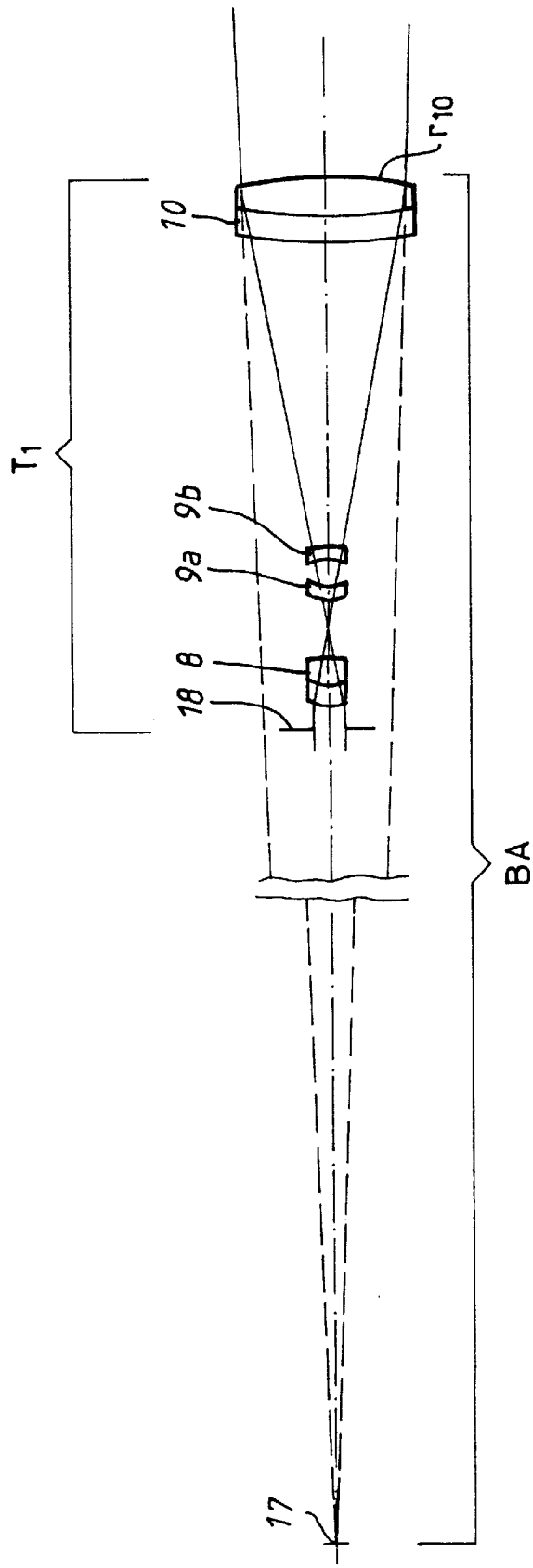
FIG. 2C shows a portion of the lens section of FIG. 2B, with the rear, virtual focal point of the proximal partial system.

The distance of the rear focal plane (17) of the proximal partial system from the distal end face (rearmost face) ($r_{10}$) of the proximal partial system ($T_1$) is shown shortened in FIG. 2C. This rear focal plane lies far in front of the left hand edge of the drawing in FIGS. 3A–3C when drawn to scale, and has a distance of −4,756 mm at an imaging scale of 1×, and of −471 mm at an imaging scale of 20×, from the distal end face ($r_{10}$) of the proximal partial system ($T_1$), and thus lies in front of the entrance plane by about 3.5 constructional lengths of the proximal component at the maximum magnification, and by about 35 constructional lengths at the minimum magnification.

The specific constructional data of a preferred embodiment of the zoom system are given in the following Table I. The surface radii of curvature, beginning with the short focal length component of the proximal partial system, are denoted by $r_i$, i=1, . . . 13, and the thicknesses or spacings between the intersection points of the respective surfaces with the optical axis are denoted by $d_i$, i=2, . . . 13. The distance of the entrance plane from the first intersection surface of the short focal length component (8) with a positive converging power is denoted by $d_1$, the distance between the intersection point of the exit face of the distal partial system ($T_2$) and the plane (14) of the cornea is denoted by $d_{14}$, and the distance between the plane (14) of the cornea and the plane (15) of the retina is denoted by $d_{15}$, all respectively measured along the optical axis. The free diameter, i.e., the dimension transverse to the optical axis, of each optical component is denoted by $d_F$.

Designations are given relating to the glass materials, under which the corresponding glasses are offered by the firm of Schott Glaswerke, Mainz.

In Table II, the focal lengths of the proximal partial system ($T_1$) for the three magnifications shown in FIGS. 3A–3C, and the respective resulting rear focal point distance (BA) of the proximal partial system from the rearmost surface ($r_{10}$) of the proximal partial system are given.

TABLE I

Magnification V = 1 ... 20

| Radius ($r_i$/mm) | Thickness or distance ($d_i$/mm) | Fr. Diam. ($d_F$/mm) | Medium |
| --- | --- | --- | --- |
| $r_1$ = 7.9433 | $d_1$ = 6.8 | 3.0 | Air |
| $r_2$ = 2.2712 | $d_2$ = 1.5 | 3.0 | SF 10 |
| $r_3$ = −3.9242 | $d_3$ = 2.0 | 3.0 | BALF 4 |
| $r_4$ = planar | $d_4$ = 9.81 ... 16.75 | 3.0 | Air |
| $r_5$ = 4.1567 | $d_5$ = 1.0 | 3.0 | F 2 |
| $r_6$ = −4.1567 | $d_6$ = 4.89 ... 9.59 | 3.0 | Air |
| $r_7$ = planar | $d_7$ = 1.0 | 3.0 | F 2 |
| $r_8$ = 131.45 | $d_8$ = 73.55 ... 61.91 | 18.0 | Air |
| $r_9$ = 38.404 | $d_9$ = 2.0 | 18.0 | SF 4 |
| $r_{10}$ = −60.866 | $d_{10}$ = 4.0 | 18.0 | SSKN 8 |
| $r_{11}$ = 66.552 | $d_{11}$ = 62.0 | 32.0 | Air |
| $r_{12}$ = −46.33 | $d_{12}$ = 8.3 | 32.0 | BALF 4 |
| $r_{13}$ = −145.913 | $d_{13}$ = 2.5 | 32.0 | SF 53 |
| Cornea (14) | $d_{14}$ = 74.13 | 32.0 | Air |
| Retina (15) | $d_{15}$ = 17.0 | | |

TABLE II

| Imaging scale | Focal length of proximal partial system ($T_1$), mm | Total focal length, mm | Rear focal point distance (BA), mm |
| --- | --- | --- | --- |
| 1 | 96.335 | −1.965 | −4755.87 |
| 10 | 9.634 | −1.273 | −761.569 |
| 20 | 4.817 | −1.058 | −471.245 |

We claim:

1. Zoom system for imaging a laser beam from a fixed entrance plane (16) onto a target plane (15) with a variable imaging scale, wherein the zoom system has a proximal partial system ($T_1$) with a variable converging power and a distal partial system ($T_2$, 12) with a fixed converging power, and a rear focal point (17) of the proximal partial system ($T_1$) is virtual and has a focal point distance (BA) that is substantially greater than its focal length.

2. Zoom system according to claim 1, wherein a front focal point of the proximal partial system ($T_1$) lies in the entrance plane (16).

3. Zoom system according to claim 1, wherein imaging of the entrance plane (16) onto the target plane (15) takes place without formation of a real intermediate image.

4. Zoom system according to claim 1, wherein an exit plane (7a) of the laser beam lies in the entrance plane (16) of the proximal partial system ($T_1$).

5. Zoom system according to claim 1, wherein the proximal partial system ($T_1$) has two lenses or lens elements (9a, 9b) with negative converging power that are displaceable parallel to an optical axis of the zoom system.

6. Zoom system according to claim 1, wherein the rear focal plane of the proximal partial system ($T_1$) is spaced from the proximal partial system by more than 5 times the focal length of the proximal partial system ($T_1$).

7. Zoom system according to claim 1, wherein the rear focal plane of the proximal partial system ($T_1$) is spaced from the proximal partial system by more than 10 times the focal length of the proximal partial system ($T_1$).

8. Zoom system according to claim 1, wherein the distal partial system ($T_2$, 12) is the objective of a slit illuminating system (3) and has a focal length between 50 mm and 200 mm.

9. Zoom system according to claim 1, wherein lens elements (8, 9a, 9b) of the proximal partial system respectively have a focal length of less than 10 mm.

10. Slit lamp microscope with laser illumination and a zoom system for the laser illumination, according to claim 1, wherein an end face (7a) of an optical fiber is arranged in the entrance plane (16) and imaged to infinity by the proximal partial system ($T_1$) of the zoom system without real intermediate imaging.

11. Slit lamp microscope according to claim to claim 10, wherein the distal partial system ($T_2$) is an objective (12) of a silt illuminating system (3), and focal lengths of the proximal partial system ($T_1$) are chosen such that a zoom regime between 1× and 20× results for the imaging of the end face (7a) of the optical fiber (7) onto a distal focal plane of the objective (12).

12. Zoom system according to claim 1, wherein the proximal partial system ($T_1$) has a distal component (10) and a proximal component (8) respectively with positive converging power, and wherein the converging power of the proximal component (8) is substantially greater than the converging power of the distal component (10).

13. Zoom system according to claim 12, wherein the converging power of the proximal component (8) with positive converging power is more than 5 times the converging power of the distal component (10).

14. Zoom system according to claim 12, wherein the converging power of the proximal component (8) with positive converging power is more than 10 times the converging power of the distal component (10).

15. Zoom system according to claim 1, having the following constructional data for system components for surface radii of curvature $r_i$/mm and thicknesses or distances $d_i$/mm and free diameter $d_f$/mm for the following optical glasses:

| Surface Radius of curvature ($r_i$/mm) | Thickness or distance ($d_i$/mm) | Free Diam. ($d_F$/mm) | Medium |
| --- | --- | --- | --- |
| $r_1$ = 7.9433 | $d_1$ = 6.8 | 3.0 | Air |
| $r_2$ = 2.2712 | $d_2$ = 1.5 | 3.0 | SF 10 |
| $r_3$ = −3.9242 | $d_3$ = 2.0 | 3.0 | BALF 4 |
| $r_4$ = planar | $d_4$ = 9.81 ... 16.75 | 3.0 | Air |
| $r_5$ = 4.1567 | $d_5$ = 1.0 | 3.0 | F 2 |
| $r_6$ = −4.1567 | $d_6$ = 4.89 ... 9.59 | 3.0 | Air |
| $r_7$ = planar | $d_7$ = 1.0 | 3.0 | F 2 |
| $r_8$ = 131.45 | $d_8$ = 73.55 ... 61.91 | 18.0 | Air |

| Surface Radius of curvature ($r_i$/mm) | Thickness or distance ($d_i$/mm) | Free Diam. ($d_F$/mm) | Medium |
|---|---|---|---|
| $r_9$ = 38.404 | $d_9$ = 2.0 | 18.0 | SF 4 |
| $r_{10}$ = −60.866 | $d_{10}$ = 4.0 | 18.0 | SSKN 8 |
| $r_{11}$ = 66.552 | $d_{11}$ = 62.0 | 32.0 | Air |
| $r_{12}$ = −46.33 | $d_{12}$ = 8.3 | 32.0 | BALF 4 |
| $r_{13}$ = −145.913 | $d_{13}$ = 2.5 | 32.0 | SF 53 |
| Cornea (14) | $d_{14}$ = 74.13 | 32.0 | Air |
| Retina (15) | $d_{15}$ = 17.0. | | |

16. Zoom system according to claim 1, having substantially the following constructional data for systems components for surface radii of curvature $r_i$ and thicknesses or distances $d_i$/mm when using the following medium for optical glasses:

| Surface Radius of curvature ($r_i$/mm) | Thickness or distance ($d_i$/mm) | Free Diam. ($d_F$/mm) | Medium |
|---|---|---|---|
| $r_1$ = 7.9433 | $d_1$ = 6.8 | 3.0 | Air |
| $r_2$ = 2.2712 | $d_2$ = 1.5 | 3.0 | SF 10 |
| $r_3$ = −3.9242 | $d_3$ = 2.0 | 3.0 | BALF 4 |
| $r_4$ = planar | $d_4$ = 9.81 ... 16.75 | 3.0 | Air |
| $r_5$ = 4.1567 | $d_5$ = 1.0 | 3.0 | F 2 |
| $r_6$ = −4.1567 | $d_6$ = 4.89 ... 9.59 | 3.0 | Air |
| $r_7$ = planar | $d_7$ = 1.0 | 3.0 | F 2 |
| $r_8$ = 131.45 | $d_8$ = 73.55 ... 61.91 | 18.0 | Air |
| $r_9$ = 38.404 | $d_9$ = 2.0 | 18.0 | SF 4 |
| $r_{10}$ = −60.866 | $d_{10}$ = 4.0 | 18.0 | SSKN 8 |
| $r_{11}$ = 66.552 | $d_{11}$ = 62.0 | 32.0 | Air |
| $r_{12}$ = −46.33 | $d_{12}$ = 8.3 | 32.0 | BALF 4 |
| $r_{13}$ = −145.913 | $d_{13}$ = 2.5 | 32.0 | SF 53 |
| Cornea (14) | $d_{14}$ = 74.13 | 32.0 | Air |
| Retina (15) | $d_{15}$ = 17.0 | | | wherein a system of comparable performance results when at least one of the above constructional data is deviated from.

* * * * *